US008591818B2

(12) United States Patent
Bokerman et al.

(10) Patent No.: US 8,591,818 B2
(45) Date of Patent: Nov. 26, 2013

(54) GAS PERMEABLE CHEMOCHROMIC COMPOSITIONS FOR HYDROGEN SENSING

(76) Inventors: Gary Bokerman, Rapid City, MI (US); Nahid Mohajeri, Rockledge, FL (US); Nazim Muradov, Melbourne, FL (US); Ali Tabatabaie-Raissi, Melbourne, FL (US)

( * ) Notice: Subject to any disclaimer, the term of this patent is extended or adjusted under 35 U.S.C. 154(b) by 1529 days.

(21) Appl. No.: 11/414,900

(22) Filed: May 1, 2006

(65) Prior Publication Data

US 2007/0224081 A1   Sep. 27, 2007

Related U.S. Application Data

(60) Provisional application No. 60/676,352, filed on Apr. 29, 2005.

(51) Int. Cl.
*G01N 31/22* (2006.01)
*G01N 21/75* (2006.01)

(52) U.S. Cl.
USPC ............ 422/94; 422/400; 422/420; 422/430; 422/87; 422/88

(58) Field of Classification Search
USPC ................... 422/400, 420–422, 424, 430, 83, 422/86–88, 94
See application file for complete search history.

(56) References Cited

U.S. PATENT DOCUMENTS

| | | | | |
|---|---|---|---|---|
| 4,212,844 A * | 7/1980 | Werner et al. | ................... | 422/56 |
| 4,362,765 A * | 12/1982 | Abe et al. | ...................... | 427/535 |
| 4,409,980 A * | 10/1983 | Yano et al. | ..................... | 600/361 |
| 5,034,189 A * | 7/1991 | Cox et al. | .......................... | 422/52 |
| 5,302,350 A * | 4/1994 | Goswami et al. | ................ | 422/86 |
| 5,511,547 A * | 4/1996 | Markle et al. | .................. | 600/348 |
| 5,665,313 A * | 9/1997 | Shimada et al. | ................. | 422/86 |
| 5,849,073 A * | 12/1998 | Sakamoto et al. | ............ | 106/437 |
| 6,395,506 B1 * | 5/2002 | Pitner et al. | ..................... | 435/32 |
| 6,773,925 B2 * | 8/2004 | Ibaraki et al. | .................. | 436/124 |
| 2002/0083883 A1 * | 7/2002 | Inoue et al. | .................. | 116/206 |
| 2003/0175004 A1 * | 9/2003 | Garito et al. | .................. | 385/143 |
| 2004/0023595 A1 | 2/2004 | Ping et al. | | |
| 2004/0037740 A1 | 2/2004 | Liu et al. | | |
| 2004/0050143 A1 * | 3/2004 | Hoagland | .................... | 73/31.05 |
| 2004/0106203 A1 * | 6/2004 | Stasiak et al. | ................... | 436/49 |
| 2004/0115818 A1 * | 6/2004 | Puri et al. | .......................... | 436/3 |
| 2004/0121478 A1 * | 6/2004 | Brinz et al. | .................... | 436/109 |
| 2005/0037512 A1 * | 2/2005 | Yeh et al. | ....................... | 436/166 |
| 2008/0193739 A1 | 8/2008 | Dickey et al. | | |

OTHER PUBLICATIONS

Smith et al. "Interfacial Stability of Thin Film Fiber-Optic Hydrogen Sensors", Proceedings of 2002 U.S. DOE Hydrogen Program Review, NREL/CP-610-32405, pp. 1-14.

(Continued)

*Primary Examiner* — Paul Hyun
(74) *Attorney, Agent, or Firm* — Jetter & Associates, P.A.

(57) ABSTRACT

A ($H_2$) sensor composition includes a gas permeable matrix material intermixed and encapsulating at least one chemochromic pigment. The chemochromic pigment produces a detectable change in color of the overall sensor composition in the presence of $H_2$ gas. The matrix material provides high $H_2$ permeability, which permits fast permeation of $H_2$ gas. In one embodiment, the chemochromic pigment comprises $PdO/TiO_2$. The sensor can be embodied as a two layer structure with the gas permeable matrix material intermixed with the chemochromic pigment in one layer and a second layer which provides a support or overcoat layer.

19 Claims, 5 Drawing Sheets

(56) References Cited

OTHER PUBLICATIONS

W.L. Robb, "Thin Silicone Membranes—Their Permeation Properties and Some Applications", Annals of the New York Academy of Sciences, 1968, 146(1), pp. 119-129.

Jeffrey F. Kramer, et al., "Low-Temperature Combustion of Hydrogen on Supported Pd Catalysts". Proceedings of the Combustion Institute. vol. 29. 2002 pp. 989-996, Department of Mechanical Engineering, University of Maryland.

Dow Corning Pressure Sensitive Solutions, Facts on File, "Guarding against potential inhibitors/poisons of platinum-catalyzed addition-cure release coatings", 2003, Dow Corning Corporation.

Dow Corning Electronics Solutions, "Information about Dow Corning Brand Adhensive/Sealants", 2005, Dow Corning Corporation.

* cited by examiner

GAS PERMEABLE CHEMOCHROMIC COMPOSITIONS FOR HYDROGEN SENSING

CROSS-REFERENCE TO RELATED APPLICATIONS

This application claims the benefit of U.S. Provisional Patent Application Ser. No. 60/676,352, entitled "GAS PERMEABLE CHEMOCHROMIC COMPOSITION FOR HYDROGEN SENSING" filed on Apr. 29, 2005, the entirety of which is incorporated herein by reference.

STATEMENT REGARDING FEDERALLY SPONSORED RESEARCH OR DEVELOPMENT

The U.S. Government may have certain rights to the invention based on NASA Grant No. NAG3-2751.

FIELD OF THE INVENTION

The invention relates to chemochromic-based hydrogen sensors.

BACKGROUND

One of the future alternatives to current fossil-based transportation fuels has been centered on hydrogen gas ($H_2$). Currently, $H_2$ is the primary energy source of today's space exploration projects (e.g., as rocket propellant). It is also used in fuel cells that power a variety of machinery including automobiles. Furthermore, hydrogen is an important industrial commodity produced and used in many industries. For example, it is used for the reduction of metal oxides (e.g. iron ore), ammonia synthesis, and production of hydrochloric acid, methanol and higher alcohols, aldehydes, hydrogenation of various petroleum, coal, oil shale and edible oils, among others. However, $H_2$ is a colorless, odorless gas, and is also a flammable gas with a lower explosive limit of about 4% in air. Therefore reliable $H_2$ sensors are required to detect possible leaks wherever $H_2$ is produced, stored, or used.

To detect $H_2$, sensors that consist of a palladium alloy Schottky diode on a silicon substrate are known. These sensors are based on metal-oxide-semiconductor (MOS) technology that is used in the semiconductor industry. The gas sensing MOS structures are composed of a hydrogen-sensitive metal (palladium or its alloy) deposited on an oxide adherent to a semiconductor. This hydrogen sensor has been commercialized and exploited in detecting $H_2$ leaks during pre-launches of space vehicles. Other research groups have also used palladium or the like as a sensing element for detecting $H_2$. A hydrogen sensor containing an array of micromachined cantilever beams coated with palladium/nickel has also been reported. Semiconductors (e.g. gallium nitride) with wide band-gap have also been used to make MOS diodes for $H_2$ detection. One of the concerns for all of these types of sensors using palladium or the like is the requirement of a high operating temperature (greater than 200° C.) and further elevated temperatures (greater than 500° C.) to reactivate the sensing element, bringing about lengthy analysis. Another issue is sensitivity of the sensing element to other compounds commonly found in the atmosphere, including water vapor, various hydrocarbons and various reducing gases such as carbon monoxide and hydrogen sulfide.

Although not conventionally used, chemochromic sensors for hydrogen sensing have been disclosed. For example, published U.S. Application No. 20040023595 to Liu et al. discloses a fast response, high sensitivity structure for optical detection of low concentrations of hydrogen gas, comprising a substrate, a water-doped $WO_3$ layer coated on the substrate; and a palladium layer coated on the water-doped $WO_3$ layer. In related work, published U.S. Application No. 20040037740 to Liu et al. discloses a sensor structure for chemochromic optical detection of hydrogen gas comprising; a glass substrate a vanadium oxide layer coated on the glass substrate; and a palladium layer coated on the vanadium oxide layer. The hydrogen sensors disclosed by Liu et al. lack field stability. Moreover, such sensors have a tendency to crack and peel, and can be washed off by precipitation and/or condensation.

U.S. Pat. No. 5,849,073 to Sakamoto discloses a pigment for sensing gas leakage which can be produced by adding at least one of the salts of platinum group metals to a slurry of particulate substrate, neutralizing the resultant mixture to deposit at least one of oxides, hydroxides and hydrated oxides of platinum group metals on the surfaces of the particulate substrate, and if necessary, further adding to said slurry at least one of compounds of aluminum, silicon, titanium, zinc, zirconium, tin, antimony and cerium, neutralizing the resultant mixture to deposit at least one of compounds such as oxides, hydroxides and hydrated oxides of aluminum, silicon, titanium, zinc, zirconium, tin, antimony and cerium, on the particles. The compositions disclosed are typically quite impervious to gas penetration. Sakamoto requires very thin coatings (typically 2 mils) with relatively high concentrations of active chemochromic compounds. In addition, compositions disclosed by Sakamoto do not show selectivity to hydrogen. Thus, there remains a need for an improved, reliable and durable chemochromic hydrogen sensor for a variety of applications, including space, transportation, oil refineries, ammonia and hydrogen plants.

SUMMARY

A hydrogen sensor is based on a composition of matter which comprises a gas permeable matrix material intermixed and encapsulating at least one chemochromic pigment, the chemochromic pigment changing color in the presence of $H_2$. In one embodiment the sensor includes a support or overcoat layer, wherein the composition is disposed on the support/overcoat layer. The support/overcoat layer can comprise a woven garment, or a silicone rubber or resin. In another embodiment, the support/overcoat layer comprises an optically transparent polymer or resin of acrylic, polycarbonate, polyurethane, cyclic olefin, styrenic copolymer, polyarylate, polyethersulfone, or polyimide containing an alicyclic structure, or an optically transparent polymer of polyester. In another embodiment, the support/overcoat layer comprises a plurality of optically transparent particles, the transparent particles having an average size less than a wavelength of visible light.

The gas permeable matrix can comprise a polymer or rubber having an oxygen permeability equal to or greater than an oxygen permeability of low density polyethylene, or a cross linked polymer, such as poly(dimethylsiloxane) rubber. The gas permeable matrix can comprise a silicone resin.

The chemochromic pigment generally comprises 1-50% by weight of the composition, such as 2-20% by weight of the composition. The composition can further comprise an accelerant or contrast additive mixed with the composition selected from $MoO_3$, $(NH_4)_6Mo_7O_{24}$, and polyoxometalates that include V, Nb, Ta, Cr, Mo, and W.

In another embodiment, a reversibility enhancing agent is encapsulated within the gas permeable matrix material, the reversibility enhancing agent selected from polyoxocompounds of W or Mo, a transition metal dopant, a metal oxide support and a solid inorganic acid.

The polyoxocompound of W or Mo can be selected from silico-tungstic acid (STA) $H_4[SiW_{12}O_{40}]$, phospho-tungstic acid (PTA) $H_3[P(W_3O_{10})_4]$, phospho-molybdic acid (PMA) $H_3[P(Mo_3O_{10})_4]$, decatungstate anion (DTA) $[W_{10}O_{32}]^{4-}$. The polyoxocompound of W or Mo can be silico-tungstic acid or phospho-tungstic acid. The support/overcoat layer can be selected from $TiO_2$, $Al_2O_3$, $SiO_2$, $ZrO_2$, and molecular sieves. The support/overcoat can comprise activated alumina.

The transition metal can be Pt, Pd, Ir, Ru, Rh or Ni. When the transition metal is platinum, the platinum can be in the form of nanoparticles having a median size in the range from 10-100 nm. The solid inorganic acid can be boric acid.

BRIEF DESCRIPTION OF THE DRAWINGS

There is shown in the drawings embodiments which are presently preferred, it being understood, however, that the invention can be embodied in other forms without departing from the spirit or essential attributes thereof.

DETAILED DESCRIPTION

Figure 1:
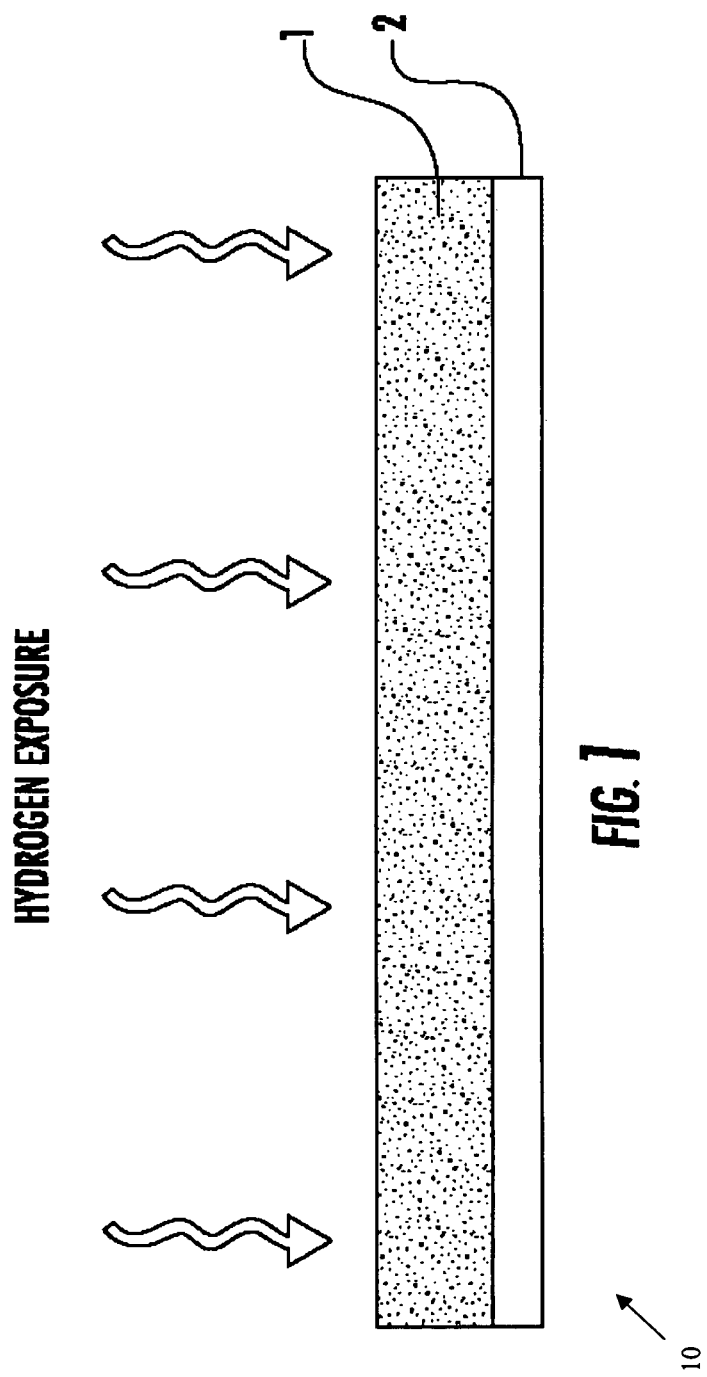
FIG. 1 shows the schematic for an exemplary two layer hydrogen sensor composite according to an embodiment of the invention.

A hydrogen ($H_2$) sensor comprises a gas permeable matrix material intermixed and encapsulating at least one chemochromic pigment. The chemochromic pigment produces a detectable change in color of the overall sensor composition in the presence of $H_2$ gas. The matrix material provides high $H_2$ permeability, which permits fast permeation of $H_2$ gas. In one embodiment, the chemochromic pigment comprises $PdO/TiO_2$.

The high gas permeability matrix material allows the composition of this invention to be used in thicker segments and with lower concentrations of the active pigment as compared to previous related sensors while retaining the rate and extent of color change similar to the free pigment. Most pigments have high water solubility. The encapsulating matrix also provides enhanced protection to weather and environmental contaminants, including those being moisture comprising, and retains that behavior at temperature extremes. For example, hydrogen detection color change using sensors according to the invention have been demonstrated at temperatures as low as −40° C.

A wide variety of gas permeable encapsulating matrix materials can be used with the invention. Preferred gas permeable polymers generally provide a gas permeability that is at least equal to the gas permeability of low-density polyethylene. The encapsulating matrix materials are preferably crosslinked polymers including silicone rubbers or silicone resins. Such polymers are water resistant which allows sensor composites according to the invention to remain useful in wet environment applications despite the water solubility of most pigments. A polysiloxane available in cross linked form that provides higher permeability to gases than other polymers is poly(dimethylsiloxane) rubber or PDMS. PDMS rubber can be prepared using a moisture cure typically referred to as a sealant, or as a high or low consistency preform of silicone rubber that is then cured to a rubbery consistency. Silicone resins are usually primarily composed of trifunctional material, so are generally highly crosslinked. Other gas permeable polymers are expected to show similar behavior, such as natural rubber and ethyl cellulose.

Cross linking is important for certain polymers for use with the invention, particularly those with low glass transition temperatures ($T_g$) relative to the intended maximum temperature of sensor operation. PDMS has a reported $T_g$ of −123° C. Polymers that have no cross linking at all become viscous flowable liquids above $T_g$. However, some cross linking renders the polymer above its $T_g$ leathery or elastomeric and thus resistant to flow. Highly cross linked polymers are strongly resistant to flow for $T>T_g$ and often provide moduli comparable to aluminum. Therefore, a polymer such as PDMS requires cross linking for use in a sensor composition according to the invention to prevent flow for operation at a temperature above its Tg, such as room temperature.

Opacity and/or transparency of the matrix material are generally preferred. Although the degree of transparency of the matrix material does not generally impact the color-changing function of pigments according to the invention, transparency of the encapsulating compound can be important in facilitating observation of the color change by naked eye where even low levels of attenuation can be of significance.

In one embodiment of the invention, $PdO/TiO_2$ or other chemochromic pigment is combined with a moisture-curing silicone sealant in the specified ratio to give a composition that responds in a very controllable way to the presence of $H_2$. The active gas sensing pigment is generally 1 to 50 wt. % of the overall composition, and is 2-20 wt. % in a preferred embodiment.

Sensor compositions according to the invention are generally applied to a solid surface, and then cured on the solid surface. In one embodiment, mixed $PdO/TiO_2$ or other chemochromic pigment mixed with silicone paste is applied to a backing sheet such as a woven glass fiber tape or possibly a woven garment. With this arrangement, only the side in contact with hydrogen will indicate the color change. U.S. Application No. 20040115818, Puri, et al. discloses an apparatus for detecting a leak site from a vessel having an inner and outer wall, comprising a chemical material response layer, and a semi-permeable layer. One of several selected semi-permeable materials is a rubbery polymer of polydimethyl siloxane. When applied in the indicated layered manner, in contrast to the admixed technique of the present invention, the one side response reported above would not occur.

Alternatively, the paste can be cast as a film on a release surface such as polytetrafluoroethylene or wax paper and then removed from the release surface after cure. After a 24-48 hour room temperature cure, the resulting film is generally rubbery and can be used directly as an indicator, which allows the color change to be viewed from either side of the sensor when overcoated. In one embodiment, the sensor composite is overcoated with additional unpigmented clear silicone as shown in the exemplary hydrogen sensor composite schematic shown in FIG. 1. The hydrogen sensor 10 includes a top layer 1 comprising PdO/TiO$_2$ pigment in a silicone matrix disposed on a clear silicone overcoat layer 2 which does not include any pigment. In a preferred embodiment, the thickness of the unpigmented silicone layer 2 is as thick as or thicker than the thickness of top layer 1 containing the pigment. With the irreversible PdO/TiO$_2$ pigment, the overcoat composition may consist of a broad range of transparent polymers and resins. They may be much less permeable materials such as acrylic, polycarbonate, polyester, polyurethane, cyclic olefin, styrenic polymer, polyarylate, polyethersulfone, and polyimide containing alicyclic structure. Additionally, the overcoat may following parameters: L*—Lightness Value, a*—position on red-green axis, and b*—position on yellow-blue axis.

$$\Delta E^* = \{(L-L')^2 + (a-a')^2 + (b-b')^2\}^{1/2}.$$

The equation above gives a standard measurement with which to compare different samples' color changes. The greater the $\Delta E^*$ value, the greater the color contrast. The chemochromic films can be analyzed both before and after exposure to hydrogen, allowing quantification of the intensity of color change.

Films prepared with pure PdO/TiO$_2$ (ISK, TiO$_2$—70%, Pd—1.0% by weight) have shown a $\Delta E^*$ value of 16.58. With the Ammonium Molybdate (AM) ISK samples ranging in ISK:AM ratios from 10:1, 5:1, the time required to complete the color change has been found to decrease with increasing concentration of AM (2.5 min to 1 min) while the intensity of the color change has been found to increase ($\Delta E^*$=19.67–18.85). The Molybdic Anhydride (MA)/ISK samples have been found to react more rapidly (all under one minute), with the intensity increasing with increased concentration of MA ($\Delta E^*$=18.83 for 10:1 ratio of ISK:MA and $\Delta E^*$=24.69 for 1:1 ratio of ISK:MA).

The color change of the H$_2$ sensor can be made to be reversible (i.e., the sensor reestablishes its original color after the exposure to H$_2$ is ceased), by incorporating reversibility enhancing agents (e.g., the compounds of transition metals that rapidly change their oxidation state and, subsequently, color in a reducing/oxidizing environment). For reversibility to proceed, it is believed that the sensor composition must allow oxidizing species, such as oxygen, to also permeate to the pigment to regenerate the original color. Crosslinked polymers including silicone rubber (e.g. PDMS rubber), when used in conjunction with the reversibility enhancing agents, have demonstrated reversibility. In such compositions, the original color is reestablished/regenerated generally within 1-30 seconds after exposure of the material to hydrogen has ceased. This behavior was demonstrated with a PDMS rubber encapsulating formulations comprising polyoxocompounds (POC) of W and/or Mo immobilized on a support and doped with small amounts of noble metals. Particular examples of POC of W and Mo include, but are not limited to: silico-tungstic acid (STA) H$_4$[SiW$_{12}$O$_{40}$], phospho-tungstic acid (PTA) H$_3$[P(W$_3$O$_{10}$)$_4$]), phospho-molybdic acid (PMA) H$_3$[P(Mo$_3$O$_{10}$)$_4$], decatungstate anions (DTA) [W$_{10}$O$_{32}$]$^{4-}$). It should be noted that STA and PTA show very fast kinetics (seconds) for both coloration and bleaching reactions, whereas PMA rapidly acquires color (seconds to minutes), but bleaches very slowly (days). Thus, depending on the particular application, the present invention provides an opportunity to fine-tune the kinetics of bleaching by changing the composition of the H$_2$ sensor formulation. Various light-colored metal oxides in the form of fine powders (0.01-100 μm) can be used as a support for the POC of W and Mo. The examples of support materials include, but are not limited to —TiO$_2$, Al$_2$O$_3$, SiO$_2$, ZrO$_2$, and molecular sieves. Activated alumina is a preferred support. Noble metal dopants such as Pt, Pd, Ir, Rh, Ru added in small quantities to the sensor formulation have been found to be generally required for enhancing the kinetics of both coloration and bleaching of POC of W and Mo. Pt is a preferred dopant; it is added to the formulation at the level of 0.001-5.0 wt. %, preferably, 0.05-1.0 wt. % (of total). The size of the Pt particles is typically in the range of 10-100 nm. The presence of Pt nano-particles (Pt$_{np}$) significantly accelerates electron transfer from molecular hydrogen to POC, e.g., STA) resulting in their rapid color change. Without Pt$_{np}$ color change would occur very slowly (hours to days), or may not occur at all. Optionally, small amounts of boric acid could be added to the reversible pigment composition. The presence of boric acid increases the surface acidity of the support material and enhances the performance of POC of W, Mo (i.e., intensifies the color change).

Although theory is not required to practice the present invention, it is believed that when H$_4$[SiW$_{12}$O$_{40}$]/Pt$_{np}$ is subjected to hydrogen, the original grayish-white color of the composition changes to dark-blue (within seconds) due to the following chemical reaction:

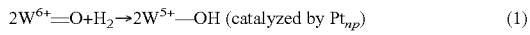
$$2W^{6+}\!=\!O + H_2 \rightarrow 2W^{5+}\!-\!OH \text{ (catalyzed by Pt}_{np}) \quad (1)$$

where, for the sake of simplicity, W$^{6+}$=O and W$^{5+}$—OH moieties represent the original (oxidized) and reduced forms of STA. The reduced form of STA absorbs light in 600-800 nm range of solar spectrum, which corresponds to a dark-blue color of the substance. After the cessation of the exposure to hydrogen flow, the original color of the sensor reappears within few seconds (for both STA- and PTA-based sensors). The bleaching of the colored sensor can be attributed to the reaction of the reduced form of STA with oxygen from air with the regeneration of the original (oxidized) form of STA as follows:

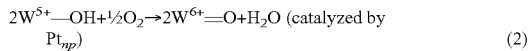
$$2W^{5+}\!-\!OH + \tfrac{1}{2}O_2 \rightarrow 2W^{6+}\!=\!O + H_2O \text{ (catalyzed by Pt}_{np}) \quad (2)$$

Control experiments indicated that reversible H$_2$ sensors according to one embodiment of the present invention are not sensitive (i.e. do not change color) upon exposure to other reducing gases such as CO, CH$_4$ and other hydrocarbons. A variety of molybdenum and tungsten compounds are expected to function similarly. It is noted that the class of reversibility enhancing agents (reversible pigments) overlaps the class of contrast additives, which, advantageously, indicates their multi-functionality. The encapsulation of the reversible chemochromic pigment in the PDMS matrix somewhat slows down the kinetics of both coloration and bleaching processes due to the diffusion limitation of H$_2$ and O$_2$ transport through the matrix material.

The invention provides a high level of selectivity to H$_2$ compared to a variety of other species. Other sensors tend to lack H$_2$ selectivity. For example, U.S. Pat. No. 5,849,073 noted above discloses that other reducing compounds will activate color change, such as carbon monoxide. Under identical conditions and in the presence of carbon monoxide, a silicone encapsulated system according to the invention did not undergo a color change, but when subjected to H$_2$ gave the usual dark color. Additional benefits are the enhanced selectivity described previously in which only the indicator side in contact with hydrogen changed color. As noted above, this effect can be reversed by overcoating to give a color change on both sides of the indicator material. This offers great potential to tailor the response to the application at hand to achieve the maximum safe hydrogen utilization environment.

The invention can be used for a variety of hydrogen sensing applications. For example, the invention can be used for smart paints, tapes and incorporated into other articles such as fabrics made used for closing, gloves, masks, and other articles to warn of $H_2$ leaks, and for applications requiring one sided and two sided responses. The invention can also be applied to fiber optic sensing heads to provide remote detection. The invention can be used for naked-eye human visual-sensing. In a preferred embodiment, sensors according to the invention can be included in automatic sensing systems, such as the sensing system shown in FIG. 1 described below.

Figure 2:
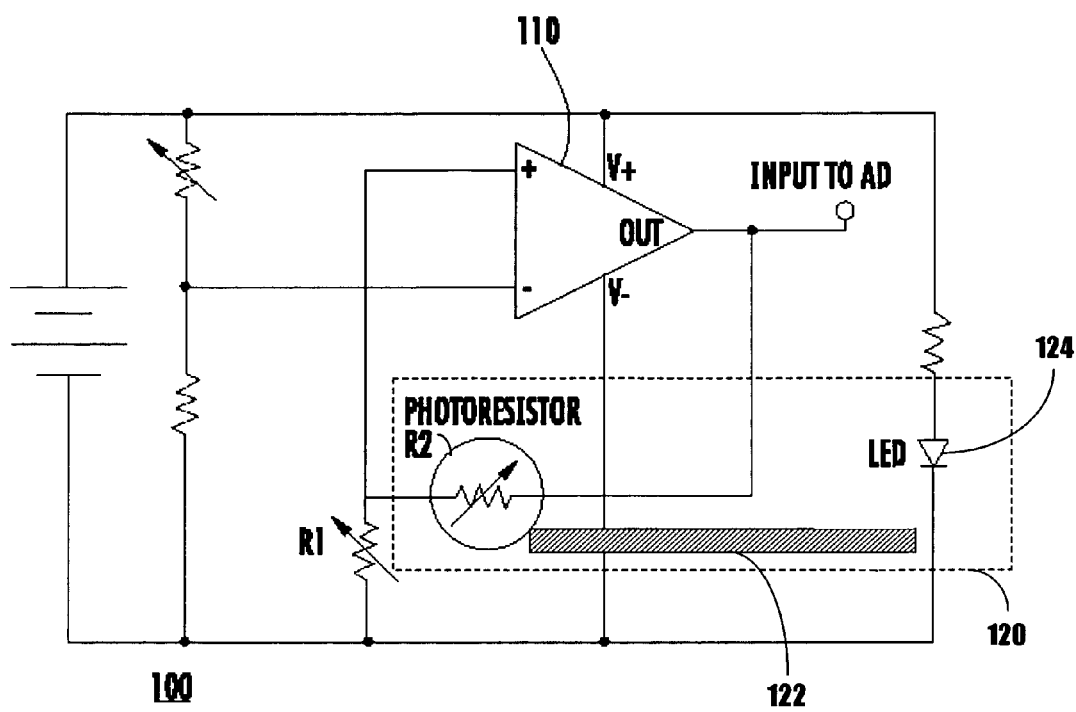
FIG. 2 shows an exemplary calorimetric $H_2$ sensor system that can be used with the invention.
Figure 3:
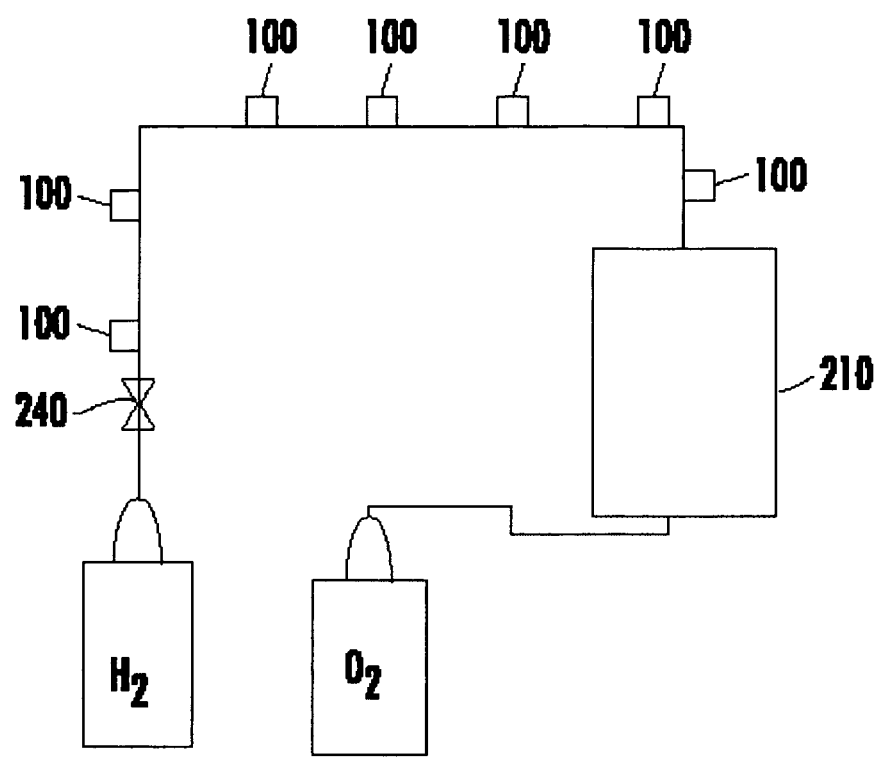
FIG. 3 shows a plurality of $H_2$ detection systems according to the invention positioned at several locations along a $H_2$ supply line which provides fuel to an electrochemical generator, such as a proton exchange membrane (PEM) fuel cell.

FIG. 2 shows an exemplary calorimetric $H_2$ sensor system that can be used with the invention. The circuit shown in FIG. 2 is not an element of the invention and is only provided to provide an exemplary sensing system that can be operated automatically and provide a measure of hydrogen concentration. The color sensor for detecting hydrogen 100 includes an op-amp 110 and a number of resistors wired as a non-inverting amplifier to provide a closed loop gain of $1+R_2/R_1$. $R_2$ is a photoresistor placed in the feedback loop of the circuit. This photo-resistor is then placed in a gas penetrable housing 120 along with a light source, such as a red LED 124, and a sensor 122 according to the invention. When light from the LED 124 is reflected off the sensor material 122, the resistance of photo-resistor $R_2$ changes based on the color of the sensor 122. The change in the value of the photoresistor $R_2$ changes the gain of the op-amp circuit. Since different colors reflect different amounts of light, a relationship between the gain of the circuit and the color of the sensor can be established. A calibration can be made using a calibrated gas flow experiment. An A/D converter (not shown) can then convert the gain into a digital output, such as an 8-bit number. After establishing what the values correspond to each color, a program can be written to automatically determine the color, the color corresponding to a hydrogen concentration.

Irreversible sensors according to the invention operate on the basis that the color change in the chemochromic material is an accumulative effect. When leaks develop beneath a chemochromic sensor/tape, the hydrogen containing stream will permeate through the sensor material containing the color changing pigments within the matrix. Since the matrix (membrane) containing the chemochromic material is a porous material, the Darcy's law applies, which states that the discharge rate (flux) q is proportional to the gradient in driving force (i.e. the difference in the partial pressures of hydrogen in either sides of the membrane, $\Delta P_{H2}$):

$$q=Q/A=-K \cdot \Delta P_{H2}/L.$$

In the above equation, Q is the flow rate of hydrogen permeating through the matrix, A is the flow cross section, K is the permeability coefficient for the membrane, and L is the membrane thickness. At the onset of the hydrogen leak and prior to the saturation and full reaction/utilization of the pigments within the matrix, the rate of hydrogen flow through the membrane will be proportional to the rate of color change: $\Delta E/\Delta t$. Therefore, before all of the pigments within the membrane have reacted, the rate of color change will be proportional to $K \cdot A \cdot \Delta P_{H2}/L$. Since the partial pressure of hydrogen at posterior membrane prior to full saturation is essentially zero, then $\Delta E/\Delta t$ is proportional to $K \cdot A \cdot P_{H2}/L$. $P_{H2}$ is the partial pressure of hydrogen at the leak surface/membrane interface (often the pressure inside the pipe, etc.). For a given membrane, K and L are constant. At a given leak location, the flow cross section A is constant. Therefore, for given situation wherein a hydrogen leak has developed, the extent of color change $\Delta E$ will be proportional to: $P_{H2} \cdot \Delta t$. $\Delta t$ refers to the length of time for the hydrogen leak through the membrane. Indeed, when colormetric measurements of a hydrogen leak were made and results were plotted against $P_{H2} \cdot \Delta t$, the data points fell on a straight line. The slope of the line is a measure of the sensitivity of the chemochromic material used as a hydrogen sensing device.

Sensors according to the invention can be integrated sensors that are fabricated on chip (e.g. Si), so that electronic components can also be on the same chip. For example, the matrix encapsulated reversible formulation can be deposited onto the end of a fiber optic thread on the chip connected to both a coherent light source and a photomultiplier that detects the intensity of light scattered back from the sensing surface. As the hydrogen diffuses, selectively, from the surroundings into the matrix and interacts with the reversible pigment resulting in color change, the change in the intensity of the back scattered light is sensed by the photomultiplier, amplified and communicated to the electronic display device.

FIG. 2 shows a plurality of $H_2$ detection systems 100 positioned at several locations along a $H_2$ supply line, which provides fuel to an electrochemical generator 210, such as a PEM fuel cell. Valve 240 when closed turns off the supply of $H_2$ to the electrochemical generator. Although not shown, the detection of $H_2$ above a predetermined level can initiate a sequence of events that closes valve 240.

EXAMPLES

The present invention is further illustrated by the following specific examples, which should not be construed as limiting the scope or content of the invention in any way.

Example 1

A small quantity of pigment (ISK Singapore, $TiO_2$—70%, Pd—1.0% wt) was mixed with an equal amount of water and applied to a clean dry microscope slide. The slide was heated to eliminate the water in preparation for contact with hydrogen. The hydrogen contact chamber consisted of a glass vacuum trap housing the microscope slide. Hydrogen gas was allowed to flow for 5 minutes before inserting the slide. After approximately 1.5 minutes of hydrogen exposure, the original beige color of the pigment changed to gray. Upon removal from hydrogen chamber, the gray color remained.

Example 2

1.01 g of ISK, $TiO_2$—70%, Pd—1.0% wt pigment was manually admixed with 9.19 g of moisture curing silicone sealant (Dow Corning R 3145 RTV Adhesive/Sealant-Clear) to give 10.2 g of material. Some of this compound was applied to a clean microscope slide and allowed to cure for 24-48 hours. This slide was then contacted with hydrogen gas as in Example 1. After approximately 1.5 minutes exposure to hydrogen gas, the original beige color of the cured compound changed to gray. Upon removal from hydrogen chamber, the gray color remained.

Example 3

A portion of the uncured pigment/sealant prepared by the method of Example 2 was applied to a piece of woven fiberglass tape. Using a draw down method with a blade, the surface of the woven fiberglass tape was covered with pigment/sealant mixture and allowed to cure. After a cure time of 24-48 hours, the flexible sheeting was ready for use as a hydrogen indicator.

Example 4

Yet another portion of the uncured pigment/sealant prepared by the method of Example 2 was used to prepare a rubber sheet indicator. A flat TEFLON™ board was lined with strips of vinyl tape to give the desired thickness to the sheet. The uncured pigment/sealant was spread on the TEFLON plate and a draw down blade was used to prepare a uniform sheet of material for curing. After 24-48 hours, a thin rubbery sheet was pealed off of the TEFLON board and used as a hydrogen indicator.

Example 5

18.0 mg of ISK, $TiO_2$—70%, Pd—1.0% wt pigment was placed within the glass U-tube of Altamira AMI-200 temperature programmed desorption (TPD) instrument. A flow of 20 ml/min of 10% $H_2$ in Argon gas was maintained through TPD's U-tube. Sample temperature within the TPD's U-tube was ramped up at a rate of 10° C./min from −100° C. to +50° C. During the temperature ramping of the sample, TPD's thermal conductivity detector (TCD) showed a signal pickup and a color change was also detected when temperatures reached −98° C. as a result of pigment reacting with the hydrogen gas.

Example 6

18.6 mg of ISK, $TiO_2$—70%, Pd—1.0% wt pigment was placed within the glass U-tube of Altamira AMI-200 TPD instrument. A flow of 20 ml/min of 10% $H_2$ in Argon gas was maintained through TPD's U-tube. Sample temperature within the TPD's U-tube was kept isothermal at −90° C. A TCD signal was detected as well as sample color change, which was attributed to the pigment reacting with $H_2$ gas. Reaction was complete in about 4 minutes.

Example 7

26.1 mg of specimen prepared according to the method of Example 4 was placed within the glass U-tube of Altamira AMI-200 TPD instrument. A flow of 20 m/min of 10% $H_2$ in Argon gas was maintained through TPD's U-tube. Sample temperature within the TPD's U-tube was kept isothermal at −30° C. A TCD signal was detected and a sample color change as well which was attributed to the pigment reacting with the hydrogen gas. Reaction was complete in less than 4 minutes.

Example 8

39.6 mg of Example 4 specimen was placed within the glass U-tube of Altamira AMI-200 TPD instrument. A flow of 20 ml/min of 5% $H_2$ in Argon gas was maintained through TPD's U-tube. Sample temperature within the TPD's U-tube was kept isothermal at −30° C. A TCD signal was detected and a sample color change as well which was attributed to the pigment reacting with the hydrogen gas. Reaction was slower than Example 7 and proceeded to completion in less than 6 minutes.

Example 9

18.2 mg of ISK, $TiO_2$—70%, Pd—1.0% wt pigment was placed within the glass U-tube of Altamira AMI-200 TPD instrument and subjected to a 20 ml/min flow of 25% CO in Argon gas. Sample temperature was ramped up at a rate of 10° C./min from −30° C. to 40° C. A TCD signal was detected as well as sample color change within a range of temperatures from −10° C. to 35° C., which is attributable to pigment reacting with CO gas and reaction was complete within 6 minutes.

Example 10

32.3 mg of ISK, $TiO_2$—70%, Pd—1.0% wt pigment was placed within the glass U-tube of Altamira AMI-200 TPD instrument and subjected to a 20 ml/min flow of 10% CO in Argon gas. Sample temperature was ramped up at a rate of 10° C./min from −30° C. to 40° C. A TCD signal was detected as well as sample color change within a temperature range of −10° C. to 35° C., which is attributable to pigment reacting with CO gas and reaction was complete within about 8 minutes.

Example 11

26.6 mg of the specimen prepared by the method of Example 4 was placed within the glass U-tube of Altamira AMI-200 TPD instrument and subjected to a 20 ml/min flow of 25% CO in Argon gas. Sample temperature was ramped up at a rate of 10° C./min from −30° C. to 45° C. No color change, as a result of CO gas reacting with the pigment, was detected.

Example 12

A sample from Example 11 was exposed to 10% $H_2$ in Argon gas using Altamira AMI-200 TPD instrument. The sample temperature was kept isothermal at −30° C. A TCD signal was detected by the instrument, which was accompanied by sample color change, similar to that of Example 7.

Example 13

17.3 mg of matrix with no pigments was placed within the glass U-tube of Altamira AMI-200 TPD instrument and subjected to a 20 ml/min flow of 10% CO in Argon gas. Sample temperature was ramped up at a rate of 10° C./min from −30° C. to 40° C. A TCD signal was detected similar to Example 10, which is attributable to dissolution of CO gas in the matrix.

Example 14

11.6 mg of ISK, $TiO_2$—70%, Pd—1.0% wt pigment was placed within the glass U-tube of Altamira AMI-200 TPD instrument and subjected to the vapors of 17.5% solution of hydrazine in water using the saturator. Two pulse chemisorption regiments were used: 50 pulses at 30° C. and 30 pulses at 60° C. In both cases no reaction or color change was detected.

Example 15

A sample of rubbery indicator sheet prepared according to the method of Example 4 was subjected to a set up simulating a leaking pipe. Two sections of stainless steel pipe with a threaded coupling were connected together loosely. One end of the line was attached to a hydrogen flow. The other end of the pipe was connected to a valve that if closed allowed hydrogen to leak out through the loose joint. A strip of the indicator sheet was wrapped around the joint and taped in place on the edge, and the hydrogen flow started. After closing the valve at the pipe's exit, hydrogen was allowed to leak through the joint for 3 minutes. The color of the exterior of the indicator sheet was beige, while the inner face of the indicator sheet turned gray. This occurred regardless of the thickness of the rubbery indicator sheet used (minimum thickness used was 2.5 mils).

Example 16

In a manner similar to Example 15, a sample of the rubbery indicator sheet of Example 4 was exposed to the hydrogen leak except that the indicator sheet was covered with SCOTCH™ tape. This resulted in the exterior face of the indicator sheet to change color from beige to gray within 1-2 minutes after exposure to hydrogen. The color of the interior face of the indicator sheet had also changed from beige to gray.

Example 17

A sample of the rubbery indicator sheet of Example 4 was immersed in water for 24 hours before use in the leaking pipe test of Example 15. This sample was evaluated as in Example 16 (Scotch tape covering). Both faces of the indicator sheet changed color within 1-2 minutes of hydrogen exposure.

Example 18

A sample of the rubbery indicator sheet of Example 4 was coated over with a layer of virgin clear silicone sealant of equal or greater thickness, and allowed to cure for 24-48 hours. The resulting cured double-layered sheet was subjected to the leaking pipe test of Example 15 by wrapping the indicator sheet with the clear overcoat around the loose pipe joint with the clear overcoat face on the exterior/outside. After 1-2 minutes of hydrogen exposure both sides of the overcoated indicator sheet had changed their color to gray.

Example 19

In another experiment, $MoO_3$ or $(NH_4)_6Mo_7O_{24}$ was added to compositions according to the invention in levels varying from equivalent to 10× the molecular content of PdO which gave a chemochromic system that showed a visually darker color upon contact with hydrogen than without the molybdenum complex and/or oxide. In addition, the extent and rate of color change also was found to significantly increase compared to that without the molybdenum complex and/or oxide.

Example 20

Several chemochromic pigments using four different $TiO_2$ support: Aldrich (mainly, $TiO_2$, rutile crystalline form) with an average particle size of 1 micron, Fisher Scientific $TiO_2$, Nanotek $TiO_2$, and P-25 Degussa nanosize $TiO_2$ were synthesized and compared to ISK, $TiO_2$—70%, Pd—1.0% wt. In a beaker, 50 mL of de-ionized (DI) water and 5.0 g of $TiO_2$ sample were mixed. With a magnetic stir bar, the mixture was continuously stirred, while heating to a temperature of 70° C. Saturated NaOH solution was used to maintain the pH at levels between 10 and 11. In a separate beaker, 10 mL of DI water, 0.25 g of $PdCl_2$, and 2.5 mL of 12N HCl were mixed. The $PdCl_2$ solution was slowly added to the support solution, carefully, to maintain the solution pH between 10 and 11. Once all of the $PdCl_2$ had been combined with the support, the pH of the solution was lowered to 8 using concentrated HCl and allowing the stirring to continue at 70° C. for one hour. After one hour, heating was stopped and the solution was filtered. The residue washed with DI water several times and placed in an oven, set at 100° C., until dry. Once dry, the sample was crushed into a powder and stored in a glass vial.

Example 21

Figure 4:
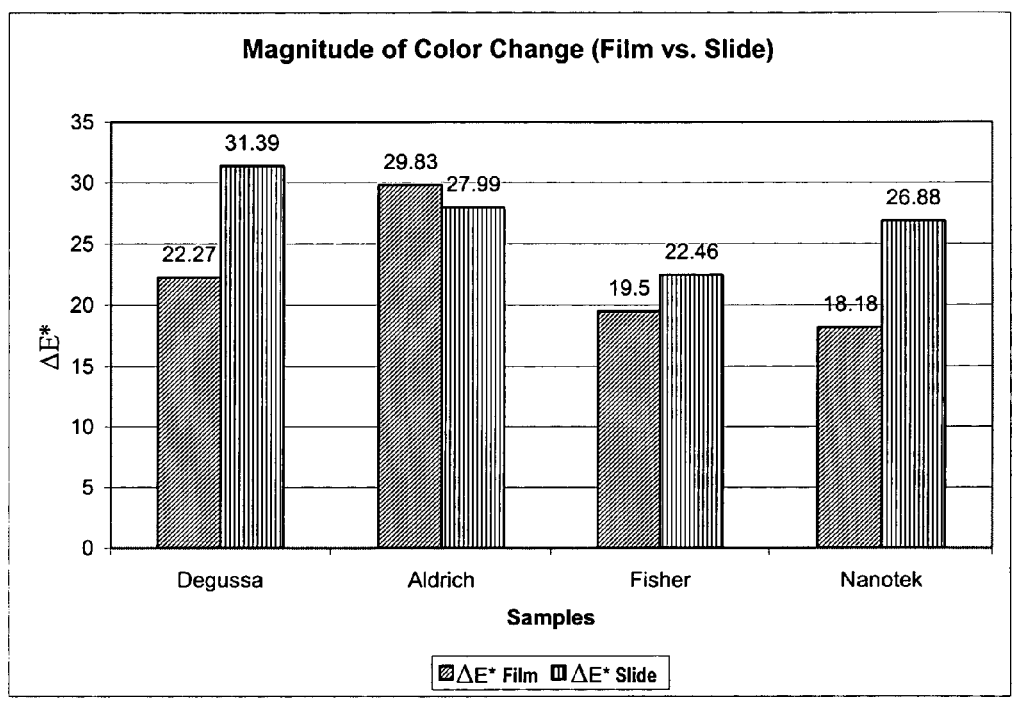
FIG. 4 depicts color contrasts measurements, $\Delta E$, for four pigments prepared in accordance with the Example 20 conducted both as a powder deposited on a glass slide (slide) and inside the RTV matrix with a pigment to matrix ratio of 1:10 (film).

Color contrasts measurements, ΔE, of the four pigments prepared in accordance with the Example 20 was conducted both as a powder deposited on a glass slide (slide) and inside the RTV matrix with a pigment to matrix ratio of 1:10 (film). Samples' colorimetric parameters $a^*$, $b^*$, $c^*$, and L were measured before and after exposure to 100% $H_2$ gas and then ΔE values were calculated. Results are shown in FIG. 4.

Example 22

An exemplary reversible $H_2$ sensor formulation formed according to an embodiment of the invention is now described. 0.5 g of $TiO_2$ powder (average particle size 25-70 nm) was mixed with 0.5 g of $H_3[P(W_3O_{10})_4]$ (Aldrich). 5 ml of the colloidal platinum solution (0.025 wt. % Pt) was added to this mixture. The colloidal Pt solution was obtained by mixing 2.5 ml of the aqueous solution of $H_2PtCl_6$ (0.1 wt. %) with 2.5 ml of the aqueous solution (0.01 wt. %) of the protective polymer (polyvinyl alcohol) followed by adding 0.1 g of sodium borohydride ($NaBH_4$) to the mixture under well-stirred conditions at room temperature until all hydrogen bubbles ceased to evolve. The $TiO_2$—$H_3[P(W_3O_{10})_4$—Pt slurry was carefully mixed and let dry overnight at ambient conditions. The resulting grayish powder was carefully mixed with 5 g of silicone sealant (Dow Corning R 3145 RTV, and the mixture was applied to the surface of a smooth sheet of perfluorinated polymer to form a thin film. After a 24-48 hour room temperature cure, the resulting rubbery film became ready for use as a reversible hydrogen sensor

Example 23

Figure 5:
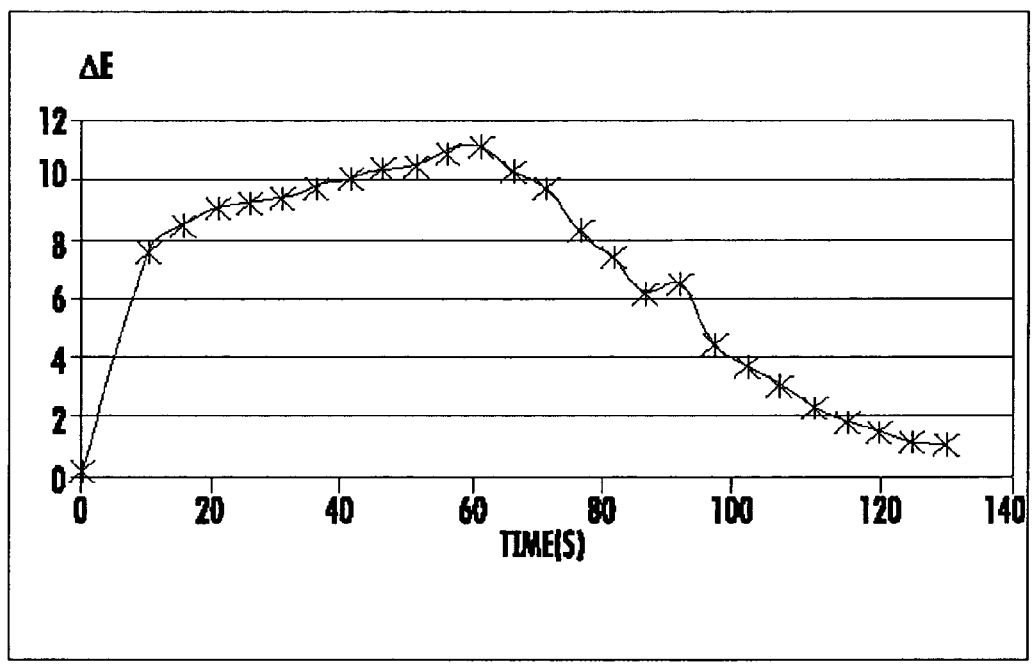
FIG. 5 depicts the kinetics of coloration and bleaching for an exemplary reversible chemochromic hydrogen sensor according to the invention.

0.6 g of activated alumina (Alltech) and 0.2 g of Pt (1 wt. %)/$Al_2O_3$ (Aldrich) was ground in an agate mortar to a fine powder (less than 100 μm). 0.8 g of silico-tungstic acid powder (Alfa Aesar) was added to the above mixture. The resulting powder was carefully mixed and ground in an agate mortar. The mixture was placed on a watch glass (about 10 cm in diameter) and 2-3 ml of distilled water was added to the powder to generate a thick slurry. The slurry was carefully mixed and left to dry overnight. After drying, the powder was crushed in an agate mortar and ground to a fine powder (less than 100 μm). The resulting powder was mixed with the silicone sealant (3145 RTV) in about 1:6 weight ratio. A thin film (about 0.5 mm) was made from the powder-sealant mixture, which was spread over a wax paper and left to cure undisturbed overnight. Resulting grayish-white tape could be easily peeled off the wax paper and used as a reversible $H_2$ sensor. FIG. 5 depicts the kinetics of coloration and bleaching using the prepared reversible $H_2$ sensor.

Example 24

In a manner like the Example 21, except that 0.4 g of boric acid powder (Aldrich) was added to the mixture of activated alumina, Pt/$Al_2O_3$ and STA. Presence of boric acid was found to intensify the coloration in the presence of hydrogen.

This invention can be embodied in other forms without departing from the spirit or essential attributes thereof and, accordingly, reference should be had to the following claims rather than the foregoing specification as indicating the scope of the invention.

We claim:

1. A hydrogen sensor, comprising:
a composite layer comprising a gas permeable crosslinked polymer intermixed and encapsulating a plurality of chemochromic pigment particles embedded therein, said plurality of chemochromic pigment particles changing color in the presence of $H_2$, wherein said plurality of chemochromic pigment particles comprise 1-50% by weight of said composite layer;
wherein said gas permeable crosslinked polymer comprises a silicone rubber or a silicone resin;
wherein said gas permeable crosslinked polymer directly contacts said plurality of chemochromic pigment particles,
and wherein said encapsulating requires said $H_2$ to be transported through said gas permeable crosslinked polymer before said plurality of chemochromic pigment particles change color in the presence of said $H_2$.

2. The sensor of claim 1, further comprising a support or overcoat layer, wherein said composite layer is disposed on said support/overcoat layer.

3. The sensor of claim 2, wherein said support/overcoat layer comprises a silicone rubber or resin.

4. The sensor of claim 2, wherein said support/overcoat layer comprises an optically transparent polymer or resin of acrylic, polycarbonate, polyurethane, cyclic olefin, styrenic copolymer, polyarylate, polyethersulfone, or polyimide containing an alicyclic structure.

5. The sensor of claim 2, wherein said support/overcoat layer comprises an optically transparent polymer of polyester.

6. The sensor of claim 2, wherein said support/overcoat layer comprises a plurality of optically transparent particles, said transparent particles having an average size less than a wavelength of visible light.

7. The sensor of claim 1, wherein said plurality of pigment particles comprise 2-20% by weight of said composite layer.

8. The sensor of claim 1, wherein said crosslinked polymer is a homopolymer.

9. The sensor of claim 1, wherein said crosslinked polymer comprises said silicone rubber.

10. The sensor of claim 1, wherein said crosslinked polymer comprises said silicone resin.

11. The sensor of claim 1, wherein said plurality of chemochromic pigment particles comprise irreversible chemochromic pigment particles.

12. The sensor of claim 1, wherein said gas permeable crosslinked polymer has an oxygen permeability equal to or greater than an oxygen permeability of low density polyethylene, and wherein said sensor is a reversible sensor.

13. The sensor of claim 12, further comprising an accelerant or contrast additive mixed with said composite layer selected from the group consisting of $MoO_3$, $(NH_4)_6Mo_7O_{24}$, and polyoxometalates that include V, Nb, Ta, Cr, Mo and W.

14. The sensor of claim 12, further comprising a reversibility enhancing agent encapsulated within said gas permeable crosslinked polymer, wherein said reversibility enhancing agent regenerates an original color of said irreversible sensor after exposure to said $H_2$ has ceased, wherein said reversibility enhancing agent is selected from the group consisting of a polyoxocompound of W or Mo, a transition metal dopant, a metal oxide support and a solid inorganic acid.

15. The sensor of claim 14, wherein said polyoxocompound of W or Mo is selected from the group consisting of silico-tungstic acid (STA) $H_4[SiW_{12}O_{40}]$, phospho-tungstic acid (PTA) $H_3[P(W_3O_{10})_4]$, phospho-molybdic acid (PMA) $H_3[P(Mo_3O_{10})_4]$ and decatungstate anion (DTA) $[W_{10}O_{32}]^{4-}$.

16. The sensor of claim 14, wherein said polyoxocompound of W or Mo is silico-tungstic acid or phospho-tungstic acid.

17. The sensor of claim 14, further comprising a support or overcoat layer, wherein said composite layer is disposed on said support/overcoat layer, said support/overcoat layer being selected from the group consisting of $TiO_2$, $Al_2O_3$, $SiO_2$, $ZrO_2$ and molecular sieves.

18. The sensor of claim 14, further comprising a support or overcoat layer, wherein said composite layer is disposed on said support/overcoat layer, said support/overcoat comprising activated alumina.

19. The sensor of claim 14 wherein said transition metal is selected from the group consisting of Pt, Pd, Ir, Ru, Rh and Ni.

* * * * *

UNITED STATES PATENT AND TRADEMARK OFFICE
CERTIFICATE OF CORRECTION

| | | |
|---|---|---|
| PATENT NO. | : 8,591,818 B2 | Page 1 of 1 |
| APPLICATION NO. | : 11/414900 | |
| DATED | : November 26, 2013 | |
| INVENTOR(S) | : Gary Bokerman et al. | |

It is certified that error appears in the above-identified patent and that said Letters Patent is hereby corrected as shown below:

In Column 1, line 13 should read as follows:

STATEMENT REGARDING FEDERALLY SPONSORED RESEARCH

This invention was made with Government support under Agency Grant No. NAG3-2751 awarded by NASA. The government has certain rights in this invention.

Signed and Sealed this
Twentieth Day of May, 2014

Michelle K. Lee
*Deputy Director of the United States Patent and Trademark Office*